(12) United States Patent
Chakravarty et al.

(10) Patent No.: US 8,282,882 B2
(45) Date of Patent: Oct. 9, 2012

(54) PHOTONIC CRYSTAL SLOT WAVEGUIDE MINIATURE ON-CHIP ABSORPTION SPECTROMETER

(76) Inventors: Swapnajit Chakravarty, Austin, TX (US); Ray T Chen, Austin, TX (US)

( * ) Notice: Subject to any disclaimer, the term of this patent is extended or adjusted under 35 U.S.C. 154(b) by 0 days.

(21) Appl. No.: 12/806,840

(22) Filed: Aug. 23, 2010

(65) Prior Publication Data

US 2012/0044489 A1    Feb. 23, 2012

(51) Int. Cl.
*G01N 21/00* (2006.01)
(52) U.S. Cl. ................................. 422/82.11; 385/12
(58) Field of Classification Search ............ 422/82.11, 422/82.09; 385/9, 12
See application file for complete search history.

(56) References Cited

U.S. PATENT DOCUMENTS

| 6,765,211 | B2 | 7/2004 | Tapalian et al. |
| 7,233,711 | B1 | 6/2007 | Beausoleil et al. |
| 7,283,712 | B2 | 10/2007 | Shaw et al. |
| 2004/0264902 | A1* | 12/2004 | Zoorob et al. ............ 385/129 |
| 2006/0285114 | A1 | 12/2006 | Cao et al. |

OTHER PUBLICATIONS

Lee M.R., Fauchet P. M., "Nanoscale microcavity sensor for single particle detection," Optics Letters vol. 32, p. 3284 (2007).
Thorpe M.J. et al, "Broadband cavity ringdown spectroscopy for sensitive and rapid molecular detection", Science vol. 311, p. 1595 (2006).
Druy M. et al, "From laboratory technique to process gas sensor: the maturation of tunable diode laser absorption spectroscopy", Spectroscopy vol. 21 iss. 3, p. 14 (2006).
Kyotoku B.B.C. et al, "Sub-nm resolution cavity enhanced microspectrometer", Optics Express vol. 18 iss. 1, p. 102 (2010).
Robinson J.T. et al, "On-chip gas detection in silicon optical microcavities," Optics Express vol. 16 iss. 6, p. 4296 (2008).
Yang W. et al, "Atomic Spectroscopy on a chip," Nature Photonics vol. 1, p. 331 (2007).
Mortensen N.A. et al, "Slow light enhancement of Beer-Lamber Bouguer absorption", Applied Physics Letters vol. 90 iss. 14, p. 141108 (2007).
Jensen K.H., "Slow light enhanced light-matter interactions with applications to gas sensing", Optics Communications vol. 281 iss. 21, p. 5335 (2008).

* cited by examiner

*Primary Examiner* — Natalia Levkovich
(74) *Attorney, Agent, or Firm* — Taboada Law Firm, PLLC; John M. Taboada

(57) ABSTRACT

Methods and systems for label-free on-chip optical absorption spectrometer consisting of a photonic crystal slot waveguide are disclosed. The invention comprises an on-chip integrated optical absorption spectroscopy device that combines the slow light effect in photonic crystal waveguide and optical field enhancement in a slot waveguide and enables detection and identification of multiple analytes to be performed simultaneously using optical absorption techniques leading to a device for chemical and biological sensing, trace detection, and identification via unique analyte absorption spectral signatures. Other embodiments are described and claimed.

16 Claims, 8 Drawing Sheets

PHOTONIC CRYSTAL SLOT WAVEGUIDE MINIATURE ON-CHIP ABSORPTION SPECTROMETER

BACKGROUND OF THE INVENTION

1. Field of the Invention

This invention relates generally to the field of optical and medical devices, and more specifically to an apparatus and method for on-chip optical spectroscopy for the detection and identification by unique spectral signatures of solid, liquid, or gas substances using photonic crystals.

2. Background of the Invention

Defect engineered photonic crystals, with sub micron dimensions have demonstrated high sensitivity to trace volumes of analytes for performing a large range of sensing applications. Photonic crystals have been described and discussed by Joannopoulos, J. D., R. D. Meade, and J. N. Winn, in *Photonic Crystals*, 1995 Princeton, N.J.: Princeton University Press. However, exact identification of analyte through spectroscopic signatures has not been demonstrated. Furthermore, much of the research in photonic crystal devices has relied on enhancing refractive index sensitivity to a single analyte (see Lee M. R., and Fauchet M., "Nanoscale microcavity sensor for single particle detection," Optics Letters 32, 3284 (2007)) and detection of a single analyte. Some of the popular commercially available optical spectroscopy techniques are cavity ringdown spectroscopy (CRDS) described by Thorpe M. J. et al., in "Broadband cavity ringdown spectroscopy for sensitive and rapid molecular detection," Science 311, 1595 (2006), and tunable diode laser absorption spectroscopy (TDLAS) described by Druy M, in "From laboratory technique to process gas sensor: the maturation of tunable diode laser absorption spectroscopy", in Spectroscopy 21(3), 14 (2006). Cavity ringdown spectroscopy cannot be integrated on-chip primarily due to the stringent requirement of optical source and high finesse optical cavities for analyte sampling. Technically, tunable diode laser absorption spectroscopy could be integrated on-chip, but the analyte sampling volume required is of the order of meters and cannot therefore be integrated on a chip. Hence tunable diode laser absorption spectroscopy is also not a convenient method to integrate on-chip. Furthermore, both cavity ringdown spectroscopy, due to the requirement of femtosecond lasers and high finesse optical cavities for high sensitivity, and tunable diode laser absorption spectroscopy, are very expensive, of the order of tens of thousands of dollars. A primary drawback of both cavity ringdown spectroscopy and tunable diode laser absorption spectroscopy is the weight, size, as well as cost which significantly increases the cost of ownership of the corresponding products. The same drawbacks of size, weight and cost hold for Fourier transform infrared spectroscopy and photoacoustic spectroscopy. A lab-on-chip integrated infrared spectrometer for remote, in-situ sensing and spectroscopic identification is highly desired for widespread deployment to enhance the detection of hazardous pollutants for environmental and homeland security. Research on on-chip spectroscopy has resulted in methods such as a ring resonator based microspectrometer described by Kyotoku B. B. C, Chen L, and Lipson M., in "Sub-nm resolution cavity enhanced microspectrometer," in Optics Express 18(1), 102 (2010) for optical spectral analysis, by Robinson J. T., Chen L, and Lipson M., in "On-chip gas detection in silicon optical microcavities," in Optics Express 16(6), 4296 (2008) for gas sensing and photonic crystal microcavity-based devices described by Canon Kabushiki Kaisha in US Patent Application 20060285114, "Gas detection and photonic crystal devices design using predicted spectral responses" which rely on the quality factor of the optical microcavity to trap light and enhance the optical interaction with the analyte by increasing the effective interaction time with the analyte with photonic crystal microcavities. However, these devices are limited by resolution of spectrometry. In order to increase the resolution of the spectrometer, either the size of the ring resonator must be increased or the number of photonic crystal microcavities must be increased in proportion to the resolution or complex grating structures need to be fabricated as described by Kyotoku B. B. C, Chen L, and Lipson M., in "Sub-nm resolution cavity enhanced microspectrometer," in Optics Express 18(1), 102 (2010). Research has been performed with hollow core waveguides for atomic spectroscopy on-chip by Yang W., Conkey D. B, Wu B, Yin D., Hawkins A. R., and Schmidt H., in "Atomic spectroscopy on a chip" in Nature Photonics 1, 331 (2007), which are limited to large sizes when the absorption cross-section of the analyte becomes small.

Two dimensional photonic crystal waveguides integrated with slot waveguides offer the possibility of integrating the slow light effect of two-dimensional photonic crystal waveguides with the optical field enhancement effect of slot waveguides to enhance the optical interaction between light and analyte. According to Beer-Lambert absorption technique, transmitted intensity I is given by equation 1 as $$I = I_0 \exp(-\gamma \alpha L) \qquad (1)$$

where $I_0$ is the incident intensity, $\alpha$ is the absorption coefficient of the medium, L is the interaction length, and $\gamma$ is the medium-specific absorption factor determined by dispersion enhanced light-matter interaction. In conventional systems, L must be large to achieve a suitable sensitivity of the measured $I/I_0$. For lab-on-chip systems, L must be small, hence $\gamma$ must be large. Mortensen et al. showed [Mortensen N. A., Xiao S. S., "Slow-light enhancement of Beer-Lambert-Bouguer absorption," Applied Physics Letters 90 (14), 141108 (2007).] using perturbation theory that $$\gamma = f \times \frac{c/n}{v_g} \qquad (2)$$

where c is the velocity of light in free space, $v_g$ is the group velocity in the medium of effective index n, and f is the filling factor denoting the relative fraction of the optical field residing in the analyte medium. Equation 2 shows that slow light propagation (small $v_g$) significantly enhances absorption. Furthermore, the greater the electric field overlap with the analyte, the greater the effective absorption by the medium. In a conventional waveguide, the optical mode interacts with the analyte only through its evanescent tail. In a slot waveguide, the guided optical mode not only interacts with the analyte environment with its evanescent tail, but also interacts with the enhanced optical field intensity in the slot. In a photonic crystal waveguide as theoretically proposed by Mortensen, only the group velocity $v_g$ is reduced. By introducing a slot in a two-dimensional photonic crystal waveguide, we have demonstrated experimentally that in a two-dimensional photonic crystal slot waveguide, the group velocity is reduced by a factor of 100 due to the slow light effect and the optical field intensity is increased by a factor of 10 in a slot compared to evanescent guiding only. As a result, the effective absorption length is increased by a factor of 1000 compared to the geometrical optical length, which increases the optical absorption by the analyte, as determined by the Beer-Lambert law of optical absorption. The factor of 1000 is much larger than the factor of 10 demonstrated by Jensen et al. using a one-dimensional Bragg stack that employs group velocity $v_g$ reduction only and has a much smaller slow light effect due to one-dimensional confinement of the slow light propagating optical mode. [Jensen K. H., Alam M. N., Scherer B, Lambrecht A., Mortensen N. A. "Slow light enhanced light-matter interactions with applications to gas sensing", Optics Communications 281 (21), 5335 (2008)]. The factor of 1000 improvement in our photonic crystal slot waveguide spectrometer due to the combined effects of high group velocity enhancement and optical intensity enhancement in a two-dimensional photonic crystal slot waveguide results in absorption lengths of the order of hundreds of microns on-chip compared to tens of centimeters in single pass off-chip spectroscopy techniques.

Spectrometer techniques such as cavity ring-down spectroscopy, ring resonator optical cavity, and photonic crystal cavity are limited in resolution, by the finesse of the optical cavity and the size and weight of the optical cavity. Designs are needed to make a miniaturized, light-weight on-chip integrated spectrometer that can measure a continuous absorption spectrum, not limited by resolution of the spectrometer.

Designs are therefore needed in the art to integrate two-dimensional photonic crystal waveguides with slot waveguides for optical absorption spectroscopy on-chip.

SUMMARY OF THE INVENTION

One embodiment of the invention provides a spectrometer comprising a semiconductor material core with high dielectric constant, supported on the bottom by a low dielectric constant cladding. A triangular lattice of photonic crystal holes is etched into the substrate. A photonic crystal waveguide is defined by filling a single row of holes, from the input ridge waveguide transition to the output ridge waveguide transition, with the semiconductor core material. A slot waveguide is similarly defined by etching a slot in the semiconductor core material and filling the photonic crystal waveguide. The high dielectric constant core with structured photonic crystal slot waveguide, together with the low dielectric constant cladding, form the photonic crystal slot waveguide structure. Light is coupled into the photonic crystal slot waveguide from a ridge waveguide. Light is out-coupled from the photonic crystal slot waveguide to an output ridge waveguide. When a broadband light source is input to the photonic crystal slot waveguide, increased absorption of light occurs due to the slow light effect of photonic crystal waveguide and enhanced optical field in the slot. Depending upon the wavelength range of interrogation, which is determined by the absorption wavelength of the analyte, the period of the sub-wavelength lattice can vary from 50 nm to 1500 nm and the depth of the lattice structure can vary from 0.4 to 0.7 times above the lattice periodicity. The semiconductor material can be silicon (or any Group IV material), gallium arsenide (or any III-V semiconductor), or any semiconductor material with high refractive index. The substrate can be any Group IV material corresponding to the Group IV core material or any substrate suitable to grow the III-V core material. A single transmission spectrum is measured in the absence of the analyte. A second transmission spectrum is measured in the presence of the analyte. The difference between the first and second transmission spectra determine the absorbance of the analyte in the interrogated wavelength range. Analyzed analytes can be pollutant gases such as greenhouse gases (carbon dioxide, carbon monoxide, methane, nitrous oxide, chlorofluorocarbons, ozone or volatile organic compound (such as benzene, toluene, xylene, ethylbenzene) vapors), hazardous gases such as ammonia, explosives such as TNT (trinitrotoluene) or RDX, by-product gases from battery off gassing in lithium ion batteries, sulfur dioxide, automobile engine exhaust, and stack exhausts in coal and oil refineries. The analyte can also be any volatile organic compounds in liquid form (such as benzene, toluene, xylene, ethylbenzene) dissolved in water. The analyte can also be solid particles or biomolecules. The optical absorption can be done at any visible, near infrared or far infrared region of the electromagnetic spectrum, to measure either overtones or fundamental vibration modes of analyte molecules in solid, liquid, or gas. To summarize:

The primary objective of the invention is to provide an on-chip integrated photonic crystal slot waveguide absorption spectrometer with compact size that can be monolithically integrated with lasers and detectors for the spectroscopic identification with unique absorption signatures of solid, liquids, and gases.

The second objective of the invention is to enable an on-chip analyte sampling cell determined by the slot dimensions in the photonic crystal slot waveguide, which enhances the optical absorption between the analyte and light over a given geometrical length on a chip, thereby eliminating the need for multiple pass absorption cells and complex optical elements employed in off-chip analyte sampling cells.

The third objective of the invention is to significantly increase the number of analytes that can be measured on an integrated chip level. Contemporary systems for measuring gases by cavity ring-down spectroscopy can measure up to 16 gases. However, the corresponding equipment can weigh approximately 100 pounds and occupy about 3 cubic feet of space. Since the present invention considers on-chip integration of photonic crystal slot waveguides that occupy less than 0.2 mm$^2$ each, dense integration of waveguides can cover the entire wavelength spectrum from the near-infrared to the far-infrared on the same silicon chip.

The fourth objective of the invention is to implement a novel spectrometer scheme on a CMOS chip that provides a continuous spectrum, where the spectrometer itself minus the detector, is not limited by resolution, as is the case for all on-chip and off-chip spectrometers.

Other objectives and advantages of the present invention will become apparent from the following descriptions, taken in connection with the accompanying drawings, wherein, by way of illustration and example, an embodiment of the present invention is disclosed.

DETAILED DESCRIPTION OF THE INVENTION

In accordance with a preferred embodiment of the present invention, a device for an on-chip integrated optical absorption spectroscopy comprises: a functional photonic crystal waveguide having a waveguide core along which light is guided, a slot at the center of the photonic crystal waveguide along the length of the photonic crystal waveguide, an input and output photonic crystal waveguide with gradually changed group index before and after the functional photonic crystal waveguide, which can bridge the refractive indices difference between conventional optical waveguides and the functional photonic crystal waveguide. The sensor can be used to detect organic or inorganic substances that can be solids and liquids. Light (from a broadband source or LED) coupled into a photonic crystal slot waveguide, in the presence of the analyte, has enhanced absorption by the analyte due to the increase in the effective optical path length caused by the enhanced field intensity in the slot and the slowdown effect of photonic crystal waveguide dispersion. Transmission spectra are measured covering the entire transmission bandwidth of the photonic crystal slot waveguide, both in the presence and absence of the analyte. The presence of the analyte leads to a decrease in transmission intensity due to absorption, compared to the transmission in the absence of the analyte. Absorbance spectrum of the analyte is determined from the difference in transmission.

In another embodiment of the present invention, a device for an on-chip integrated optical absorption spectroscopy comprises: a functional photonic crystal waveguide having a waveguide core along which light is guided, a slot at the center of the photonic crystal waveguide along the length of the photonic crystal waveguide, an input and output photonic crystal waveguide with gradually changed group index before and after the functional photonic crystal waveguide, which can bridge the refractive indices difference between conventional optical waveguides and the functional photonic crystal waveguide. The top cladding is air in which the analyte of interest must be detected. The sensor can be used to detect presence of pollutant gases such as greenhouse gases (carbon dioxide, carbon monoxide, methane, nitrous oxide, chlorofluorocarbons, ozone or volatile organic compound (such as benzene, toluene, xylene, ethylbenzene) vapors), hazardous gases such as ammonia, explosives such as TNT (trinitrotoluene) or RDX, by-product gases from battery off gassing in lithium ion batteries, sulfur dioxide, automobile engine exhaust, stack exhausts in coal and oil refineries. Light (from a broadband source or LED) coupled into a photonic crystal slot waveguide, in the presence of the analyte, has enhanced absorption by the analyte due to the increase in the effective optical path length caused by the enhanced field intensity in the slot and the slowdown effect of photonic crystal waveguide dispersion. Transmission spectra are measured covering the entire transmission bandwidth of the photonic crystal slot waveguide, both in the presence and absence of the analyte. The presence of the analyte leads to a decrease in transmission intensity due to absorption, compared to the transmission in the absence of the analyte. Absorbance spectrum of the analyte is determined from the difference in transmission.

In another embodiment of the present invention, a device for an on-chip integrated optical absorption spectroscopy comprises: a functional photonic crystal waveguide having a waveguide core along which light is guided, a slot at the center of the photonic crystal waveguide along the length of the photonic crystal waveguide, an input and output photonic crystal waveguide with gradually changed group index before and after the functional photonic crystal waveguide, which can bridge the refractive indices difference between conventional optical waveguides and the functional photonic crystal waveguide. The top cladding is a layer of organic polymer such as PDMS (poly-dimethyl-siloxane) or PMMA (poly-methyl methyl-acrylate) that is hydrophobic but readily swells in the presence of volatile organic compounds such as benzene, toluene, xylene or ethylbenzene. The polymer which forms the top cladding also fills the photonic crystal holes as well as the slot in the middle of the photonic crystal slot waveguide. Light (from a broadband source or LED) coupled into a photonic crystal slot waveguide, in the presence of the analyte, has enhanced absorption by the analyte due to the increase in the effective optical path length caused by the enhanced field intensity in the slot and the slowdown effect of photonic crystal waveguide dispersion. Due to the water filtering capability of the hydrophobic polymer, only the volatile organic compound contaminants in the water are absorbed by the polymer; light is guided in the photonic crystal slot waveguide and transmission spectra are measured without interference from the strong absorption signatures of water. Transmission spectra are measured covering the entire transmission bandwidth of the photonic crystal slot waveguide, both in the presence and absence of the analyte, in this case the volatile organic compounds, in the water. The presence of the analyte leads to a decrease in transmission intensity due to absorption, compared to the transmission in the absence of the analyte. Absorbance spectrum of the analyte is determined from the difference in transmission, without interference of the water medium in which the analyte of interest is located.

For the measurement of environmental parameters in situ, the device is incorporated with a filter to remove macroscopic dirt and dust particles and moisture. The filter can be a macroscopic filter incorporated off-chip or a microfluidic filter incorporated on-chip.

For the measurement of environmental parameters in-situ from remote distances, the device is incorporated with a optical fiber to couple light into and out of the chip. The spectrometer can also be monolithically integrated with semiconductor chip based lasers and detectors, that emit and detect at the absorbance wavelengths of interest of the target gas, and the device can be operated using wireless signals. No line-of-sight based limitations exist for the invention for measuring at remote distances in-situ in tight spaces, such as those in quantum cascade laser based open-path and retro-reflector systems.

For the measurement of different substances that have absorbance characteristics in different regions of the electromagnetic spectrum, due to the scalability of Maxwell's equations, the device can simply be scaled geometrically in proportion to wavelength without altering the ratio of semiconductor core material and empty space, called the filling fraction of the semiconductor core material. The filter can be a macroscopic filter incorporated off-chip or a microfluidic filter incorporated on-chip.

Methods for fabricating photonic crystal slot waveguide structures are widely described in the literature. The amount of absorption and hence the change in transmission intensity is determined by the concentration of analyte, the absorption cross-section of analyte, the wavelength of interrogation (whether near-infrared or far-infrared), the harmonic that is interrogated (whether fundamental vibrations or overtones) and the geometrical length of the photonic crystal slot waveguide.

On-chip optical spectrometers provide an unprecedented opportunity for comprehensive concurrent analysis of thousands of analytes such as hazardous gases and pollutants, greenhouse gases, explosive gases, biomolecules, contaminant solids and liquids. The spectroscopic analysis response to a toxic agent, provides a more unique signature of the toxicologically significant substance. The spectrometers have utility in the fields of industrial process control and monitoring, homeland security, environmental protection, and bio- and chemical warfare defense.

The principles of the invention can also be applied to tunable diode laser absorption spectroscopy incorporating a photonic crystal slot based optical waveguide. The enhanced optical absorption enabled by slow light and slot enhancement, when combined with the principles of tunable diode laser absorption spectroscopy using either wavelength modulation or frequency modulation, will enable on-chip optical absorption spectroscopy, for highly sensitive lab-on-chip spectroscopy. In such cases, the tunable laser/light emitter wavelength that coincides with the absorption signature of the analyte of interest is guided over the bandwidth of the slow light region in the photonic crystal slot waveguide and the analyte sampled by the slot in the middle of the photonic crystal slot waveguide.

BRIEF DESCRIPTION OF THE DRAWINGS

The drawings constitute a part of this specification and include exemplary embodiments of the present invention, which may be embodied in various forms. It is to be understood that in some instances various aspects of the present invention may be shown exaggerated or enlarged to facilitate an understanding of the invention.

A more complete and thorough understanding of the present invention and benefits thereof may be acquired by referring to the following description together with the accompanying drawings, in which like reference numbers indicate like features, and wherein.

DETAILED DESCRIPTIONS OF THE PREFERRED EMBODIMENTS

Detailed descriptions of the preferred embodiments are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

A lab-on-chip integrated infrared spectrometer for remote, in-situ sensing and spectroscopic identification of hazardous pollutants in the environment, specifically greenhouse gases, is highly desired. Defect engineered photonic crystals, with sub micron dimensions have already demonstrated high sensitivity to trace volumes of analytes. However, exact identification of analyte through spectroscopic signatures has not been demonstrated. Our photonic crystal slot waveguide device combines the slow light effect in photonic crystal waveguides with large optical field intensity in a low index slot at the center of the photonic crystal waveguide to enhance interaction between the optical field and the analyte gas. Transmission spectrum of photonic crystal slot waveguide is measured in presence and absence of methane gas and absorbance determined from difference in transmission. The waveguide is fabricated on a silicon-on-insulator wafer with standard complementary metal oxide semiconductor (CMOS) fabrication steps. Our generic on-chip spectrometer will enable low cost on-chip chemical and biological analysis and diverse applications in industrial process control and monitoring. This section will provide detailed description of the preferred embodiments in the aspect of device architecture, as well as the design concept, and working principle.

Figure 1:
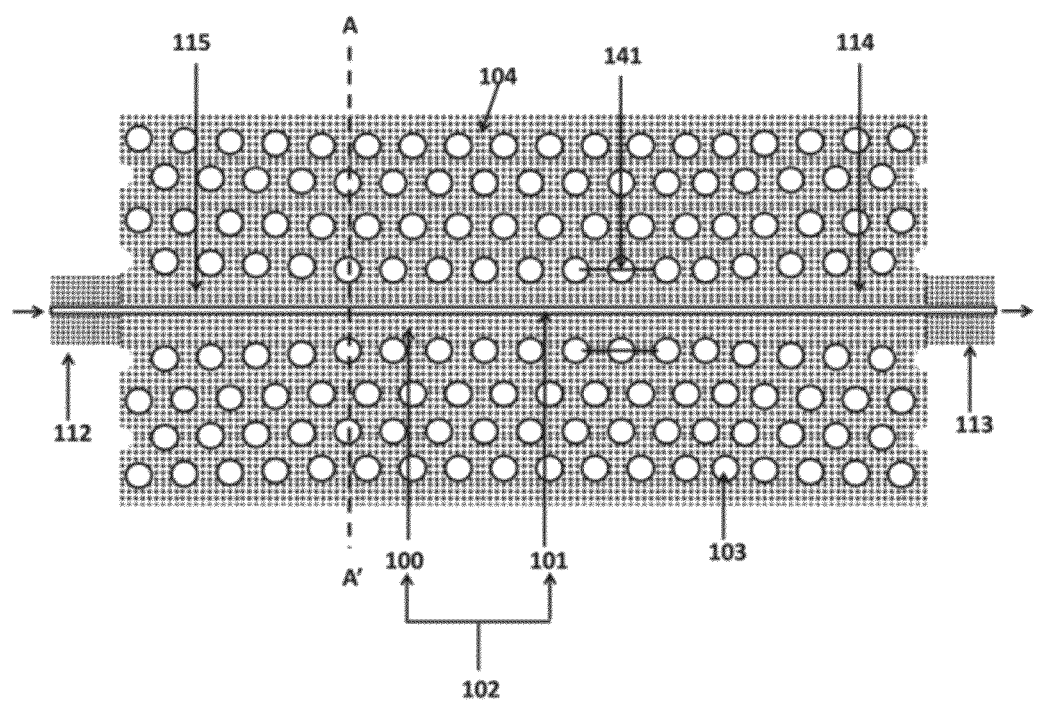
FIG. 1 is a top view schematic drawing showing the design of a photonic crystal slot waveguide based on a slot integrated with a photonic crystal waveguide.
Figure 2:
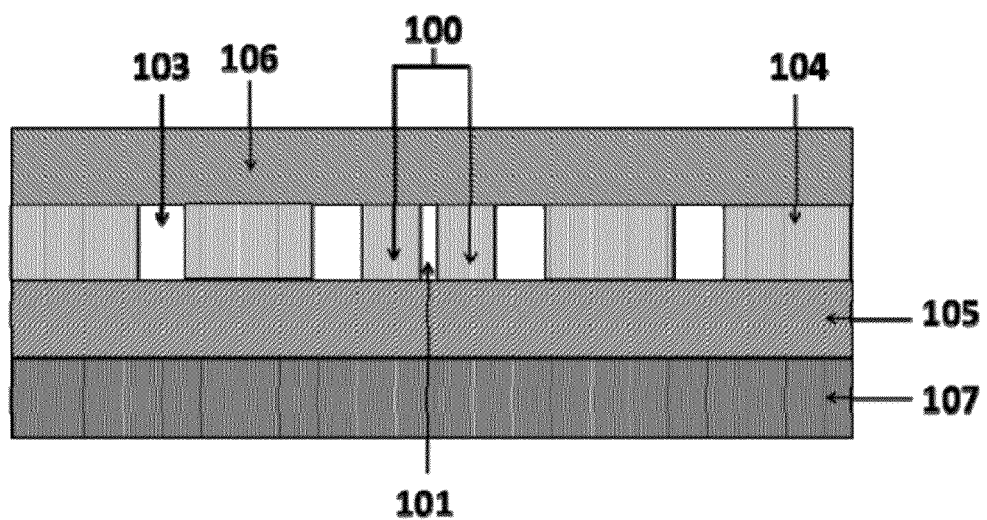
FIG. 2 is a cross-sectional view of the device shown in FIG. 1 taken along line A-A'.

FIG. 1 presents a schematic drawing of a photonic crystal slot waveguide. It consists of a functional photonic crystal waveguide 100, input ridge waveguide 112, output ridge waveguide 113 and a slot 101 extending from input to output. The combination of photonic crystal waveguide 100 and slot 101 is designated as the functional photonic crystal slot waveguide 102. The functional photonic crystal slot waveguide 102 includes a number of column members 103 etched through or partially into the semiconductor slab 104. The waveguide core 141 is defined as the space between the centers of two column members adjacent to the region where the columns are absent. In one preferred embodiment, the column members 103 are arranged to form a periodic lattice with a lattice constant α. In some embodiments, the width of waveguide core 141 can range from sqrt(3)/2 to 50 sqrt(3) times the lattice constant or period α. The arrows indicate the direction in which electromagnetic waves are coupled into and out of the photonic crystal waveguide respectively. The photonic crystal waveguide 100 is defined by filling a complete row of columnar members with the semiconductor slab material 104. The slot 101 is etched into the photonic crystal waveguide 100. The width of the slot 101 can range from an infinitesimally narrow width of 10 nanometers or smaller as limited by any lithography method to as large as the width of the waveguide core 141. The number of slots 101 can vary from one (1) to infinity, solely determined by the number that can be accommodated in the width of the photonic crystal waveguide 100, thereby creating either a photonic crystal single slot or multiple slot waveguide. With reference to FIG. 2, which is a cross-sectional view of the functional photonic crystal slot waveguide 102 in FIG. 1 taken along line A-A', the column members 103 extend throughout the thickness of the slab 104 to reach a bottom cladding 105. In one embodiment, the top cladding 106 is air. The material of the top cladding also fills the column members 103 and the slot 101 in the middle of the photonic crystal slot waveguide 102. However, one skilled in the art will note that the material which constitutes the top cladding 106 and fills the column members 103 and slot 101, can be any hydrophobic organic material such as PDMS (poly-dimetyl siloxane) or PMMA (poly-methyl methylacrylate) that absorbs and swells in the presence of organic contaminants in water and at the same time, does not absorb water. One skilled in the art will note that the material which constitutes the top cladding 106 and fills the columnar members 103 and slot 101 can be any other organic or inorganic dielectric material that suitably isolates the analyte whose absorption spectrum is to be measured, from the background medium, when the absorption spectrum of the analyte to be measured is small and can be masked by the overlapping absorption signatures of the background medium. Columnar members 103 can extend through both 106 and 104 as well as through the bottom cladding 105 to reach the substrate 107. One skilled in the art will also realize that the top cladding 106 can extend either finitely or infinitely in the vertical direction, perpendicular to the slab 104. When the top cladding 106 extends finitely, and it is desired to obtain the analyte spectrum independent of the background medium, the thickness of the top cladding 106 must be sufficient so that the tail of optical mode which propagates down the photonic crystal slot waveguide does not interact with the background medium. Although the structure within the slab 104 is substantially uniform in the vertical direction in this embodiment, one skilled in the art will understand that vertically non-uniform structure, such as the columnar members 103 whose radii are varying along the vertical direction, may be used as well. The column members 103 can be either simply void or filled with other dielectric materials. Between the ridge waveguide 112 and the core photonic crystal slot waveguide 102, there is an impedance taper 115 for coupling of light from the ridge waveguide to the photonic crystal slot waveguide with high efficiency. Similarly, at the output, between the photonic crystal slot waveguide 102 and the output ridge waveguide 113, there is another impedance taper 114 for better coupling efficiency. The waveguides are tapered by shifting the columnar members by x times α in the direction perpendicular to 100, in the plane of the waveguide, where α is the lattice constant and x varies from 0.05 to 0.4 in steps of 0.05, from the photonic crystal waveguide to the ridge waveguide. For a photonic crystal waveguide 100, 114 and 115, which comprise photonic crystals of two-dimensional periodicity, the wave guiding in the vertical direction must be provided by conventional index-guiding scheme. This means a bottom cladding 105 and a superstrate 106 with a lower effective index relative to that of the slab material must be disposed below and above the slab 104. In FIG. 2, the superstrate is 106 and simply represented by air or vacuum. The superstrate 106 can also be any organic or inorganic material. On one side, bottom cladding 105 and superstrate 106 prevent guided lightwave escaping far away from the top and bottom surfaces of the slab 104. In most applications, it is desirable that the waveguide have a single guided mode, which can be achieved through adjusting the width of waveguide core 141.

Figure 3:
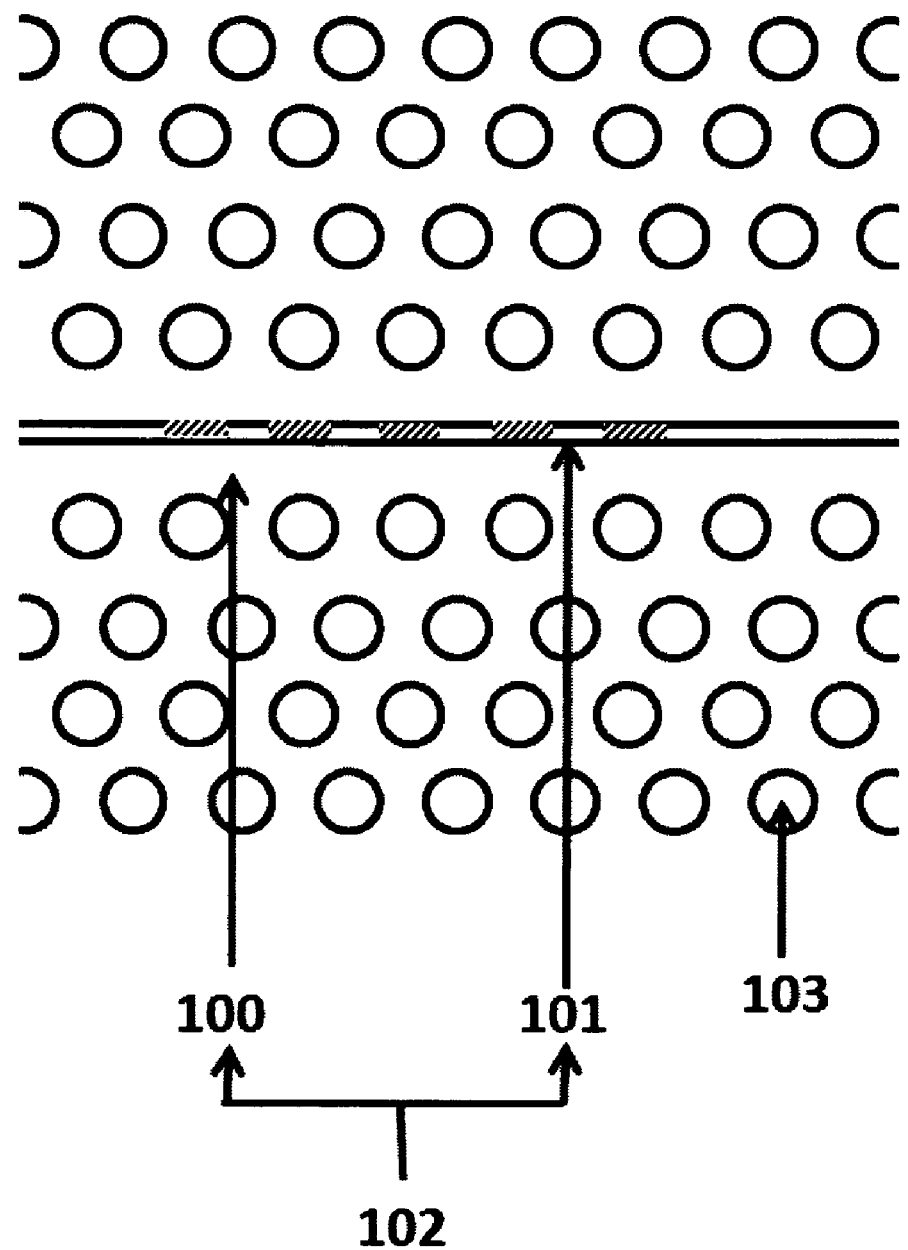
FIG. 3 is a top view of the field intensity pattern of a guided mode of a photonic crystal slot waveguide depicted in FIG. 1 and FIG. 2.

FIG. 3 depicts a top view of the field intensity pattern of a guided mode of a photonic crystal slot waveguide 102 in FIG. 1 and FIG. 2. The circles indicate columnar members 103 of the photonic crystal waveguide. It is seen in FIG. 3 that peak of the field intensity is well confined inside the slot 101 of the photonic crystal slot waveguide 102 in the core region 141.

Figure 4A:
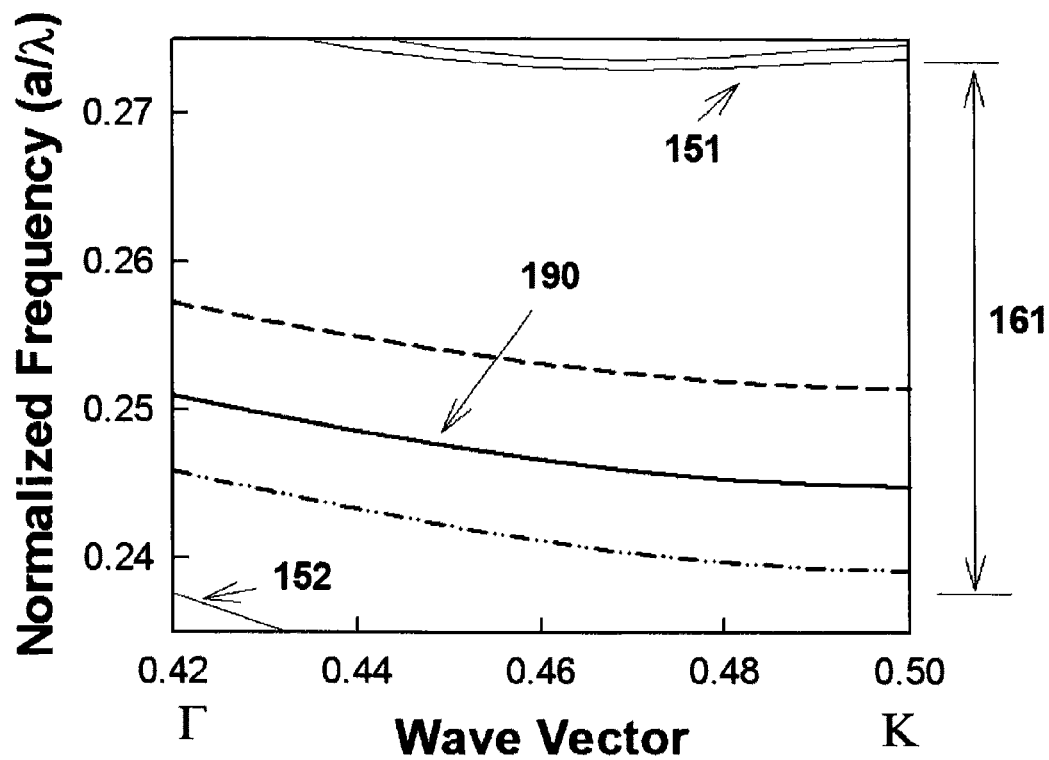
FIGS. 4a and 4b illustrate typical diagrams of the dispersion relation of a photonic crystal slot waveguide in the low group velocity region.
Figure 4B:
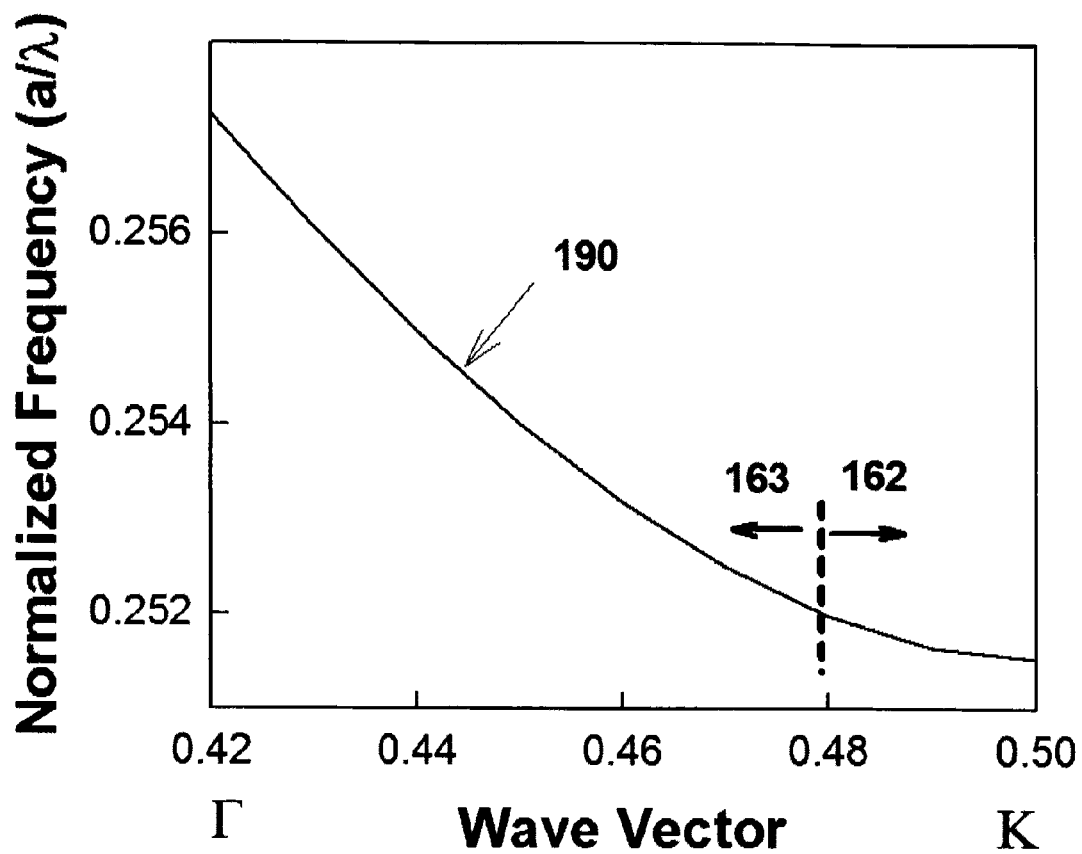

The bold curve 190 in FIG. 4a depicts a dispersion diagram of the photonic crystal slot waveguide 102. Based on design requirements, the dispersion curve 190 can be shifted up or down in frequency, as shown in FIG. 4a, by adjusting the width of the photonic crystal waveguide region 100 or the width of the slot 101 constituting the photonic crystal slot waveguide 102. The width of the region 100 can be varied as x times sqrt(3) multiplied by the lattice constant. Typically, x is varied from 0.6 to 1.4. However, one skilled in the art will note that x can be any factor that gives rise to a photonic crystal slot waveguide mode confined in the photonic band gap 161, the region between the air band 151 and dielectric bands 152 as shown in FIG. 4a. One skilled in the art will also note that the width of the slot 101 can range from an infinitesimally narrow width of 10 nanometers or smaller as limited by any lithography method to as large as the width of the waveguide core 141, that gives rise to a photonic crystal slot waveguide mode confined in the photonic band gap 161, the region between the air band 151 and dielectric bands 152 as shown in FIG. 4a. FIG. 4b shows one of the curves 190 for a waveguide with x equal to 0.9?. Two regions are distinctly visible in the bold curve, a region 163 where dω/dk is high and a region 162 where dω/dk is low. dω/dk denotes the group velocity of light propagating in the photonic crystal waveguide at the corresponding frequency. Region 162 is the design frequency range in a tunable diode laser absorption spectroscopy, tunable laser absorption spectroscopy or tunable light emitter absorption spectroscopy on-chip device. The region 161 denotes the bandgap of the photonic crystal waveguide. The enhancement of optical absorption is inversely proportional to the group velocity, consequently the slower the group velocities, the higher the enhancement of optical absorption by the analyte filling the slot 101 in the photonic crystal slot waveguide 102.

Figure 5A:
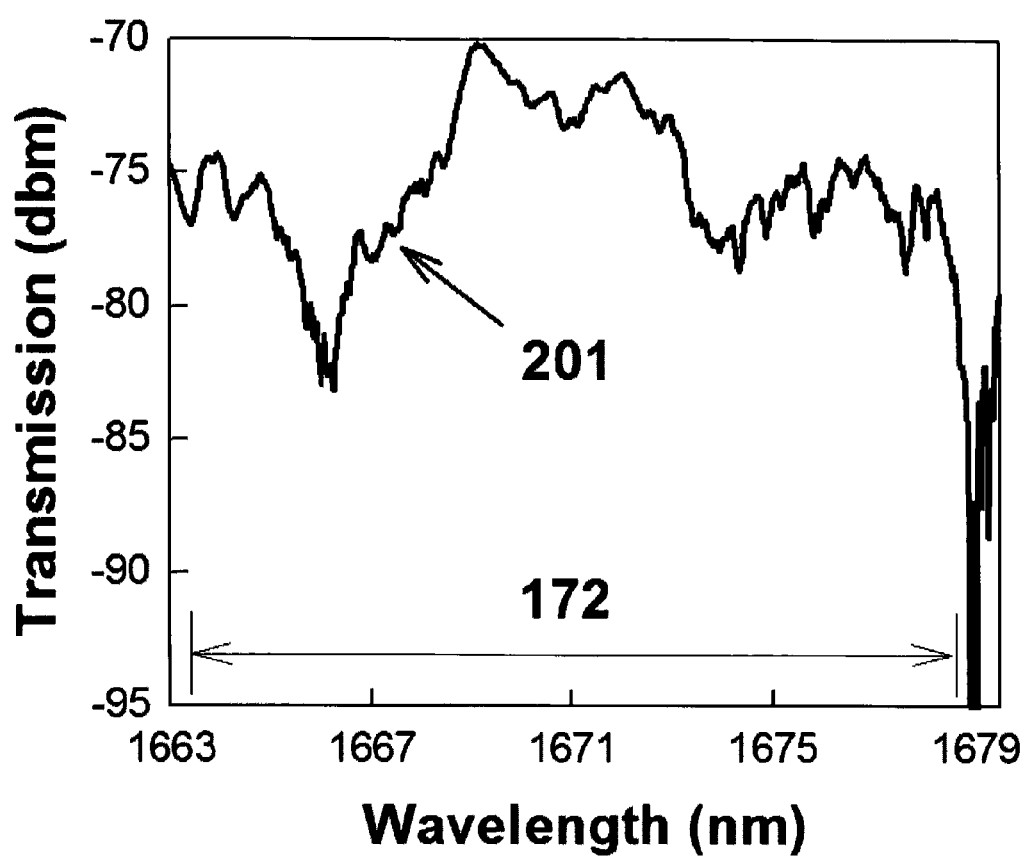
FIG. 5a shows the experimental transmission spectrum of a functional photonic crystal slot waveguide in the absence of methane as a representative analyte, as a function of wavelength.
Figure 5B:
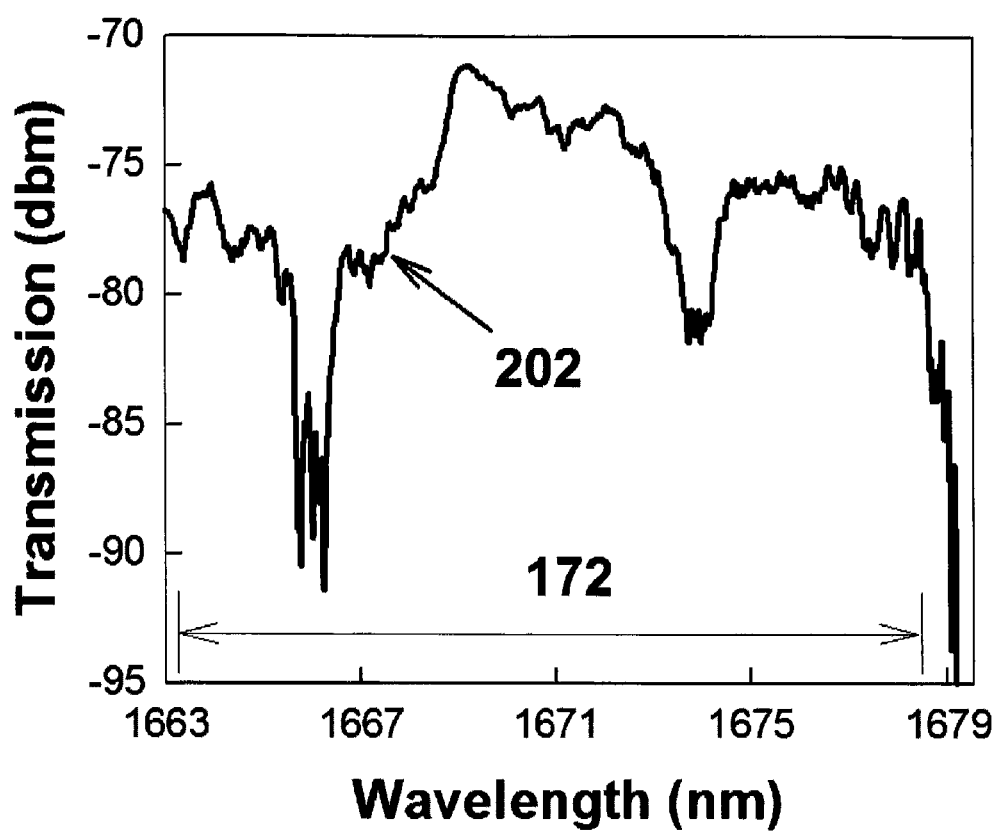
FIG. 5b shows the experimental transmission spectrum of a functional photonic crystal slot waveguide in the presence of methane as a representative analyte, as a function of wavelength.
Figure 5C:
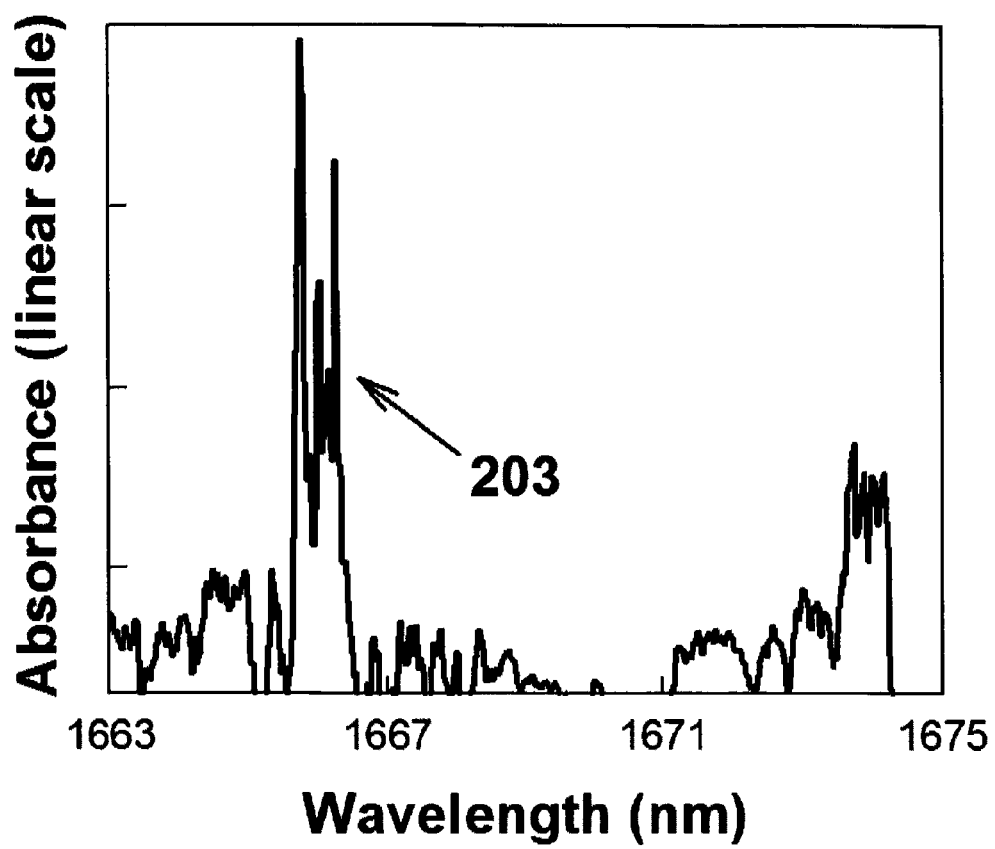
FIG. 5c shows the difference spectrum which determines the absorbance characteristics of the analyte, in this case, methane gas as a function of wavelength.

The bold curve 201 in FIG. 5a depicts the transmission spectrum of the photonic crystal slot waveguide device in the absence of methane gas as a representative analyte, over the wavelength range from 1663 nm to 1679.5 nm. Corresponding to the slow light region or low group velocity region 162 in the dispersion diagram in FIG. 4b, the slow light region or region of low group velocity in the transmission spectrum is shown as 172. The sharp drop in the transmission spectrum at about 1679 nm corresponds to the band edge of the photonic crystal waveguide. The bold curve 202 in FIG. 5b depicts the transmission spectrum of the photonic crystal slot waveguide device in the presence of methane gas as a representative analyte, over the wavelength range from 1663 nm to 1679.5 nm. Corresponding to the slow light region or region of low group velocity region 162 in the dispersion diagram in FIG. 4b, the slow light region or region of low group velocity in the transmission spectrum is shown as 172. The sharp drop in the transmission spectrum at about 1679 nm corresponds to the band edge of the photonic crystal waveguide. The bold curve 203 in FIG. 5c depicts the difference of the transmission spectra 201 and 202 of the photonic crystal slot waveguide device in the absence and presence of methane gas respectively, that determines the absorbance of methane over the wavelength range 1663 nm to 1675 nm. The spectrum of FIG. 5c shows very good correspondence with the theoretically calculated spectrum of methane in the range of 1666 nm [HITRAN spectroscopic database, Rothman et al., "The HITRAN 2008 molecular spectroscopic database," J. Quantitative Spectroscopy and Radiative Transfer 110, 533 (2009)]. However, one skilled in the art will note that the analyte can be any solid, liquid, or gas and the range of wavelength can be any range in the entire electromagnetic spectrum (ultraviolet, visible, infrared (near-, mid- and far-)), which displays absorption signatures of that corresponding specific solid, liquid, or gas.

In one embodiment, the slab 104 is formed from a material of high refractive index including, but not limited to, silicon, germanium, carbon, gallium nitride, gallium arsenide, gallium phosphide, indium nitride, indium phosphide, indium arsenide, zinc oxide, zinc sulfide, silicon oxide, silicon nitride, alloys thereof, metals, and organic polymer composites. Single crystalline, polycrystalline, amorphous, and other forms of silicon may be used as appropriate. Organic materials with embedded inorganic particles, particularly metal particles, may be used to advantage. In one embodiment, the top cladding 106 and bottom cladding 105 are formed from a material whose refractive index is lower than that of the slab material. Suitable top cladding and bottom cladding materials include, but not limited to, air, silicon dioxide, silicon nitride, alumina, organic polymers and alloys thereof. The substrate 107 materials include, but not limited to, silicon, gallium arsenide, indium phosphide, gallium nitride, sapphire, glass, polymer and alloys thereof. In one embodiment, the columnar members 103 are formed from a material whose refractive index is substantially different from that of the slab 104. Suitable materials for the columnar members 103 include, but not limited to, air, silicon oxide, silicon nitride, alumina, organic polymers, or alloys thereof. In one preferred embodiment, the slab 104 is formed from silicon, the columnar members 103 are formed from air, the top cladding 106 is air, and the bottom cladding 105 is formed from silicon dioxide, while the substrate 107 is silicon.

Although the word "analyte" is used in the preceding discussions, one skilled in the art will understand that it refers to a general form of analyte that includes, solids, liquids, and gases.

Although the word "light" or "lightwave" is used to denote signals in the preceding discussions, one skilled in the art will understand that it refers to a general form of electromagnetic radiation that includes, and is not limited to, visible light, infrared light, ultra-violet light, radio waves, and microwaves.

In summary, the present invention provides an ultra-compact on-chip spectrometer using a two-dimensional photonic crystal slot waveguide. The invention will lay a solid foundation for the future of on-chip spectroscopy devices for label free massively parallel detection and identification of analytes in lab-on-chip applications. Owing to the small dimensions of the devices presented herein, one can monolithically integrate the photonic crystal slot waveguide spectrometers on silicon VLSI chips. The CMOS compatible photonic crystal slot waveguide devices have simpler design requirements than the microelectronics industry. Furthermore, easy regeneration capability, less complicated optics, on-chip slot waveguide analyte sampling cell, and on-chip integration ensures that our miniature compact devices will deliver improved results with significantly lower cost to the customer. The device will enable low cost on-chip chemical and biological analysis and diverse applications in industrial process control and monitoring, homeland security, and environmental pollution monitoring.

While the invention has been described in connection with a number of preferred embodiments, it is not intended to limit the scope of the invention to the particular form set forth, but on the contrary, it is intended to cover such alternatives, modifications, and equivalents as may be included within the design concept of the invention as defined by the appended claims.

What is claimed is:

1. An apparatus for on-chip optical absorption spectroscopy comprising:
    a substrate;
    a bottom cladding disposed on the substrate;
    a slab disposed on the bottom cladding, wherein the refractive index of the bottom cladding is lower than the refractive index of the slab;
    a plurality of void columnar members etched through the slab, wherein the plurality of void columnar members form a periodic lattice with a lattice constant $\alpha$;
    a core in the slab comprising an input side on a first end of the slab and an output side on a second end of the slab;
    a photonic crystal slot waveguide comprising:
        a photonic crystal waveguide formed within the core by a row of void columnar members from the input side to the output side, wherein the row of void columnar members is filled with the material of the slab; and
        one or more slot waveguides defined by one or more void slots within the photonic crystal waveguide, extending the entire length of the photonic crystal waveguide;
    an input impedance taper in the photonic crystal waveguide at the input side of the photonic crystal waveguide in the plane of the slab, wherein the input impedance taper is formed by one or more void columnar members from the input side shifted away and normal to the photonic crystal waveguide and adjacent the length of both sides of the photonic crystal waveguide;
    an input ridge waveguide in the core coupled to the input impedance taper in the photonic crystal waveguide, in the plane of the slab;
    an output impedance taper in the photonic crystal waveguide at the output side in the plane of the slab, wherein the output impedance taper is formed by one or more void columnar members from the output side shifted away and normal to the photonic crystal waveguide and adjacent the length of both sides of the photonic crystal waveguide;
    an output ridge waveguide in the core coupled to the output impedance taper in the photonic crystal waveguide, in the plane of the slab;
    the one or more void slots within the photonic crystal slot waveguide extend into the input impedance taper, the input ridge waveguide, the output impedance taper, and the output ridge waveguide;
    wherein the photonic crystal slot waveguide supports one or more guided modes and further comprises a region where the electric field intensity of a guided light is enhanced and the group velocity of the guided light is lowered; and
    wherein the output transmission spectrum intensity of the guided light varies as a function of the absorbance of an analyte within the photonic crystal slot waveguide.

2. The apparatus of claim 1, wherein the periodic lattice comprises a triangular lattice or a square lattice.

3. The apparatus of claim 1, the apparatus further comprising:
    a superstrate, wherein the refractive index of the superstrate is lower than the refractive index of the slab.

4. The apparatus of claim 1, wherein the input impedance taper is formed by the first eight void columnar members shifted from the input end by x times $\alpha$, where x ranges from 0.4 to 0.05 in decrements of 0.05 and wherein the output impedance taper is formed by the first eight void columnar members shifted from the output end by x times $\alpha$, where x ranges from 0.4 to 0.05 in decrements of 0.05.

5. The apparatus of claim 1, wherein the material of the slab is selected from the group consisting of: silicon, germanium, carbon, gallium nitride, gallium arsenide, gallium phosphide, indium nitride, indium phosphide, aluminum arsenide, zinc oxide, silicon dioxide, silicon nitride, alloys thereof, and organic polymers.

6. The apparatus of claim 1, wherein the plurality of void columnar members is filled with material selected from the group consisting of: air, silicon dioxide, silicon nitride, and organic polymers.

7. The apparatus of claim 1, the apparatus further comprising an analyte disposed within the one or more void slots.

8. The apparatus of claim 7, wherein the effective absorbance of the guided light by the analyte is directly proportional to the enhancement of the electric field intensity of the one or more guided modes.

9. The apparatus of claim 7, wherein the effective absorbance of the guided light by the analyte is inversely proportional to the group velocity of the one or more guided modes.

10. The apparatus of claim 1, wherein the guided light ranges from ultraviolet to far infrared.

11. The apparatus of claim 1, the apparatus further comprising:
    an on-chip light emitter configured to emit light into the core; and
    an on-chip light detector configured to detect the output transmission spectrum intensity of the guided light.

12. The apparatus of claim 3, wherein the superstrate, the one or more void slots, and the plurality of void columnar members are filled with a hydrophobic polymer or any material that selectively absorbs an analyte from a background medium.

13. The apparatus of claim 11, wherein the on-chip light emitter comprises a light emitting diode or a semiconductor laser and the on-chip light detector comprises a photodiode;

wherein the on-chip light emitter and the on-chip light detector are configured for remote in-situ operation via wireless signals.

14. The apparatus of claim 7, the apparatus further comprising a filter configured to filter out particles from the analyte and wherein the filter comprises an on-chip microfluidic filter or an off-chip macroscopic filter.

15. The apparatus of claim 7, the apparatus further comprising a filter configured to absorb the moisture of the analyte.

16. The apparatus of claim 11, wherein the on chip light emitter is frequency or wavelength modulated.

* * * * *